United States Patent
Prior et al.

(10) Patent No.: US 11,730,467 B2
(45) Date of Patent: *Aug. 22, 2023

(54) VAGINAL TISSUE CLOSURE

(71) Applicant: Covidien LP, Mansfield, MA (US)

(72) Inventors: Scott J. Prior, Shelton, CT (US); Thomas E. Drochner, Longmont, CO (US); Michael B. Lyons, Boulder, CO (US)

(73) Assignee: Covidien LP, Mansfield, MA (US)

( * ) Notice: Subject to any disclaimer, the term of this patent is extended or adjusted under 35 U.S.C. 154(b) by 413 days.

This patent is subject to a terminal disclaimer.

(21) Appl. No.: 16/943,595

(22) Filed: Jul. 30, 2020

(65) Prior Publication Data

US 2020/0352560 A1    Nov. 12, 2020

Related U.S. Application Data

(63) Continuation of application No. 15/882,252, filed on Jan. 29, 2018, now Pat. No. 10,751,044.
(Continued)

(51) Int. Cl.
*A61B 17/04* (2006.01)
*A61B 1/303* (2006.01)
(Continued)

(52) U.S. Cl.
CPC .......... *A61B 17/0469* (2013.01); *A61B 1/303* (2013.01); *A61B 17/0482* (2013.01);
(Continued)

(58) Field of Classification Search
CPC . A61B 17/0469; A61B 17/0483; A61B 17/29; A61B 17/062; A61B 17/06166; A61B 17/0482; A61B 17/42; A61B 17/0487; A61B 1/303; A61B 2090/309; A61B 2017/308; A61B 2017/0414; A61B 2017/0472; A61B 2017/06176;
(Continued)

(56) References Cited

U.S. PATENT DOCUMENTS 3,946,740 A   3/1976   Bassett
5,037,021 A   8/1991   Mills
(Continued)

FOREIGN PATENT DOCUMENTS

CN    2917679 Y    7/2007
CN    201664332 U   12/2010
(Continued)

OTHER PUBLICATIONS

Partial European Search Report issued in European Application No. 18154596.3 dated Jun. 19, 2018.

*Primary Examiner* — Julian W Woo
(74) *Attorney, Agent, or Firm* — Carter, DeLuca & Farrell LLP

(57) ABSTRACT

A tissue closure system for closing vaginal tissue includes a tissue closure device having an end effector supporting one or more sutures securable to vaginal tissue. The one or more sutures may be separated from the end effector and tied to the vaginal tissue. The tissue closure system may include a tissue approximation device configured to apply negative pressure to vaginal tissue for approximating portions of the vaginal tissue together.

11 Claims, 9 Drawing Sheets

Related U.S. Application Data

(60) Provisional application No. 62/453,747, filed on Feb. 2, 2017.

(51) Int. Cl.
   *A61B 17/42* (2006.01)
   *A61B 17/06* (2006.01)
   *A61B 17/062* (2006.01)
   *A61B 17/29* (2006.01)
   *A61B 17/00* (2006.01)
   *A61B 17/30* (2006.01)
   *A61B 90/30* (2016.01)

(52) U.S. Cl.
   CPC ...... *A61B 17/0483* (2013.01); *A61B 17/0487* (2013.01); *A61B 17/062* (2013.01); *A61B 17/06166* (2013.01); *A61B 17/29* (2013.01); *A61B 17/42* (2013.01); *A61B 17/0057* (2013.01); *A61B 2017/0065* (2013.01); *A61B 2017/0414* (2013.01); *A61B 2017/0417* (2013.01); *A61B 2017/0464* (2013.01); *A61B 2017/0472* (2013.01); *A61B 2017/0488* (2013.01); *A61B 2017/06176* (2013.01); *A61B 2017/308* (2013.01); *A61B 2017/4216* (2013.01); *A61B 2090/309* (2016.02)

(58) Field of Classification Search
   CPC .... A61B 2017/0417; A61B 2017/0464; A61B 17/0057; A61B 2017/0488; A61B 2017/4216; A61B 2017/0065
   See application file for complete search history.

(56) References Cited

U.S. PATENT DOCUMENTS

| | | | |
|---|---|---|---|
| 5,041,101 A | 8/1991 | Seder et al. | |
| 5,478,344 A | 12/1995 | Stone et al. | |
| 5,540,705 A | 7/1996 | Meade et al. | |
| 5,769,791 A | 6/1998 | Benaron et al. | |
| 5,860,985 A | 1/1999 | Anschutz | |
| 6,004,332 A | 12/1999 | Yoon et al. | |
| 6,143,005 A | 11/2000 | Yoon et al. | |
| 6,165,183 A | 12/2000 | Kuehn et al. | |
| 6,224,614 B1 | 5/2001 | Yoon | |
| 7,220,266 B2 | 5/2007 | Gambale | |
| 7,776,057 B2 | 8/2010 | Laufer et al. | |
| 8,057,386 B2 | 11/2011 | Aznoian | |
| 8,100,920 B2 | 1/2012 | Gambale | |
| 8,882,785 B2 | 11/2014 | DiCesare | |
| 9,717,524 B2 * | 8/2017 | Hayashida | A61B 17/42 |
| 10,751,044 B2 | 8/2020 | Prior et al. | |
| 11,154,327 B2 * | 10/2021 | Richey | A61B 1/00096 |
| 11,484,331 B2 * | 11/2022 | Goldfarb | A61B 17/29 |
| 2002/0040226 A1 | 4/2002 | Laufer et al. | |
| 2003/0023250 A1 | 1/2003 | Watschke et al. | |
| 2003/0078599 A1 | 4/2003 | O'Quinn et al. | |
| 2003/0083674 A1 | 5/2003 | Gibbens | |
| 2004/0260314 A1 | 12/2004 | Lizardi | |
| 2005/0015101 A1 | 1/2005 | Gibbens et al. | |
| 2005/0113634 A1 | 5/2005 | Burbank et al. | |
| 2006/0069396 A1 | 3/2006 | Meade et al. | |
| 2006/0281970 A1 | 12/2006 | Stokes et al. | |
| 2008/0140091 A1 | 6/2008 | DeDeyne et al. | |
| 2009/0012538 A1 | 1/2009 | Saliman | |
| 2009/0138029 A1 | 5/2009 | Saliman et al. | |
| 2011/0022063 A1 | 1/2011 | McClurg et al. | |
| 2011/0245825 A1 | 10/2011 | Mitzlaff et al. | |
| 2012/0109159 A1 | 5/2012 | Jordan et al. | |
| 2012/0116416 A1 | 5/2012 | Neff et al. | |
| 2013/0023906 A1 | 1/2013 | Kubalak | |
| 2013/0225936 A1 | 8/2013 | Alexander et al. | |
| 2015/0282835 A1 | 10/2015 | Castro et al. | |

FOREIGN PATENT DOCUMENTS

| | | |
|---|---|---|
| CN | 203042401 U | 7/2013 |
| CN | 205072992 U | 3/2016 |
| EP | 1832237 A1 | 9/2007 |
| EP | 2862521 A1 | 4/2015 |
| WO | 2010114634 A1 | 10/2010 |
| WO | 2015093239 A1 | 6/2015 |
| WO | 2016025132 A1 | 2/2016 |

* cited by examiner

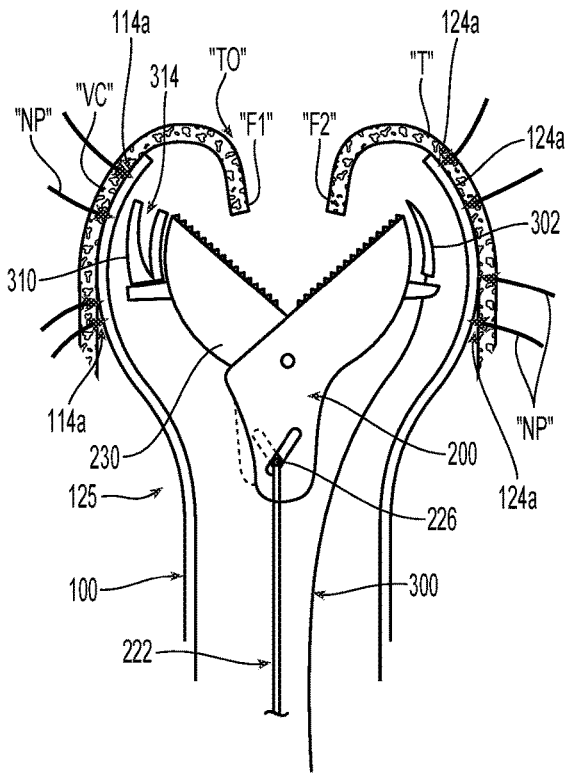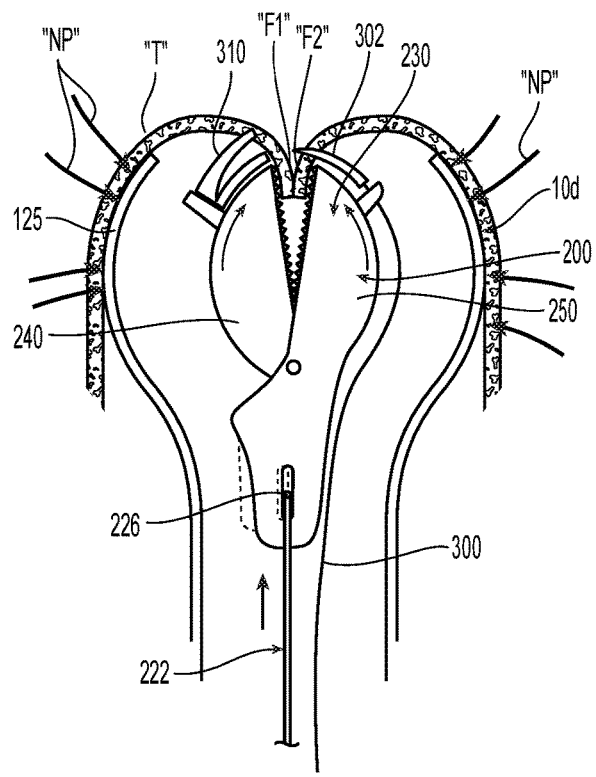
Fig. 4A  Fig. 4B
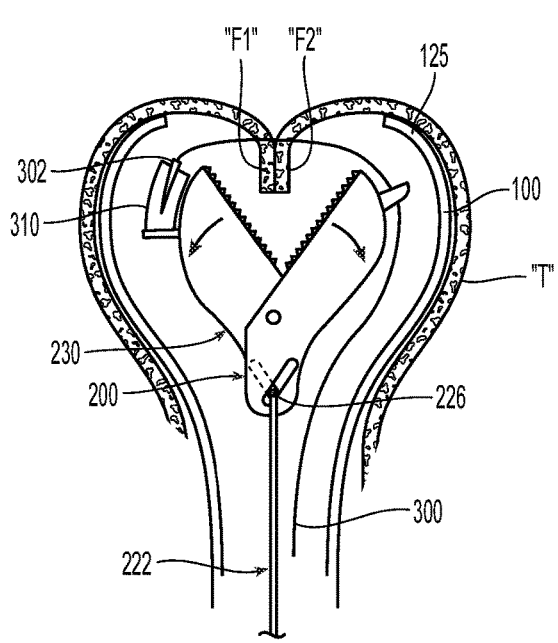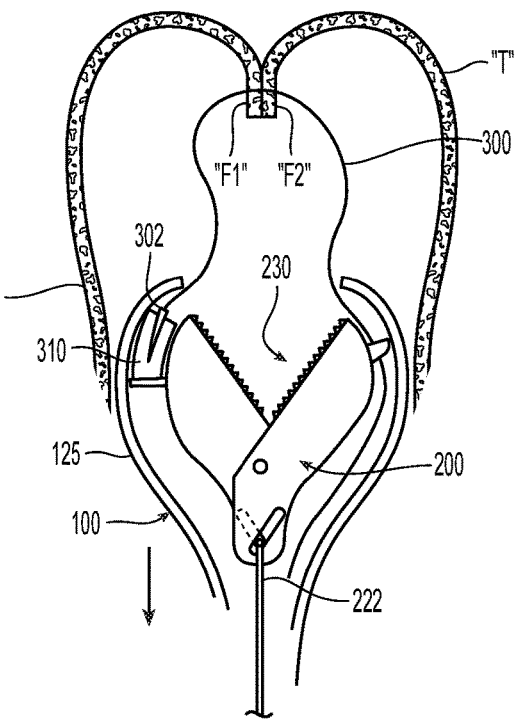
Fig. 4C  Fig. 4D

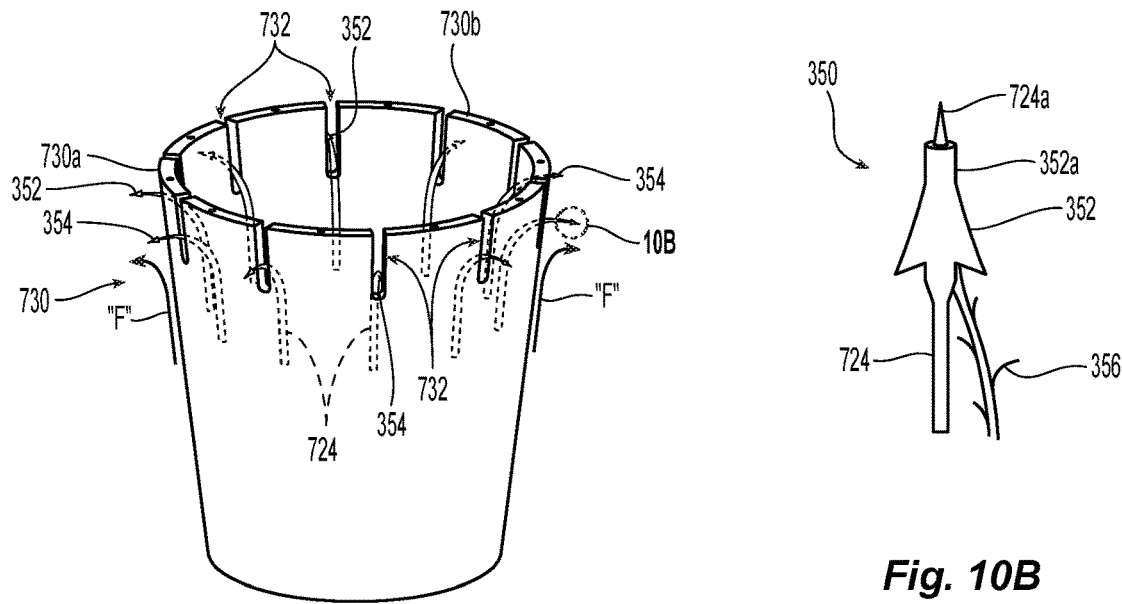
Fig. 10A
Fig. 10B
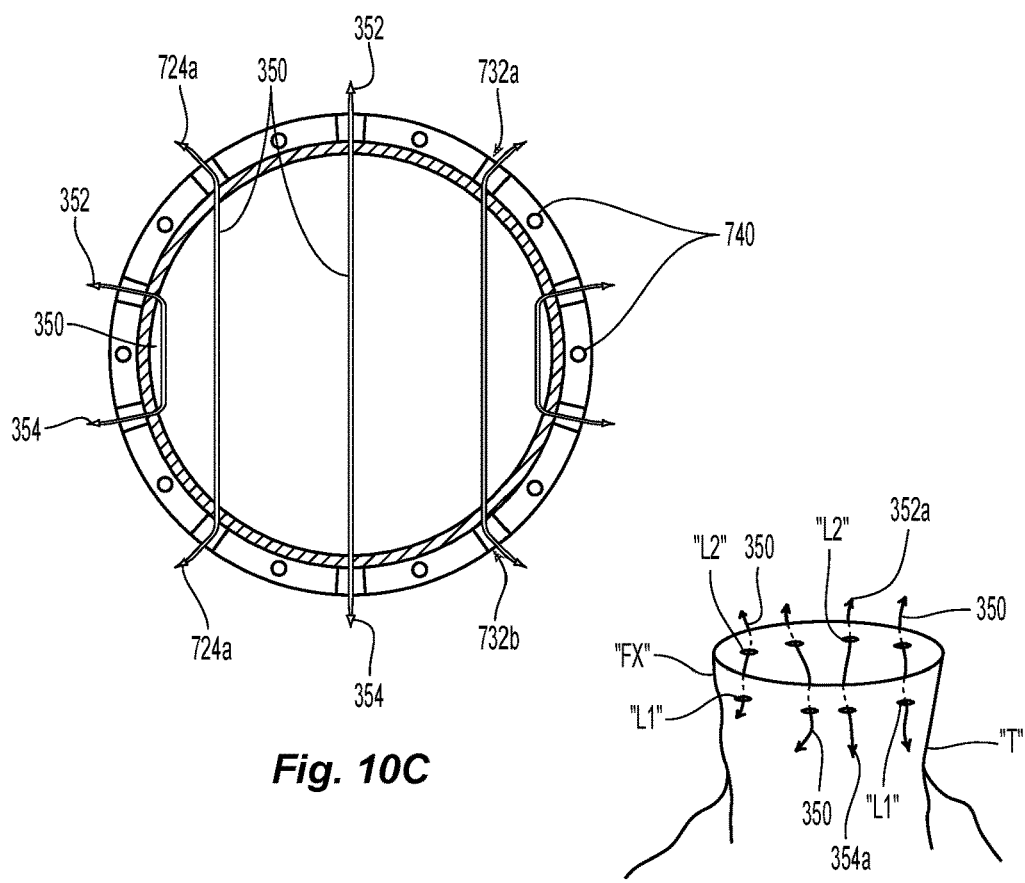
Fig. 10C
Fig. 11

VAGINAL TISSUE CLOSURE

CROSS REFERENCE TO RELATED APPLICATIONS

The present application is a continuation of U.S. patent application Ser. No. 15/882,252, filed on Jan. 29, 2018, which claims the benefit of U.S. Provisional Application Ser. No. 62/453,747, filed on Feb. 2, 2017, the entire contents of each of which are incorporated herein by reference.

TECHNICAL FIELD

The present disclosure relates to tissue closure and, more particularly, to systems, devices, and methods for closing tissue, such as vaginal cuff tissue, which may have been incised or opened in connection with a colpotomy and/or hysterectomy procedure.

BACKGROUND

Approximately 4 million hysterectomies are performed per year worldwide, and virtually all of them require a closure of the vaginal cuff. Closure of the vaginal cuff can be a tedious procedure requiring proper stitch placement and spacing while avoiding inadvertent injury to critical structures. If the vaginal cuff is not properly closed (e.g., by suture), complications of vaginal cuff dehiscence may arise. In certain circumstances, vaginal cuff dehiscence may even lead to abdominal tissue evisceration.

SUMMARY

Accordingly, a need exists to provide systems, devices, and/or methods for improving vaginal cuff closure and limiting the risks associated with vaginal cuff dehiscence.

In accordance with an aspect of the present disclosure, a vaginal tissue closure system is provided. The vaginal tissue closure system includes a tissue approximation device and a tissue closure device. The tissue approximation device defines a longitudinal axis and has a paddle. The paddle is movable relative to the longitudinal axis and includes a suction aperture defined therein. The suction aperture is configured to apply negative pressure to vaginal tissue to maintain the tissue in close proximity to the paddle as the paddle moves relative to the longitudinal axis. The tissue closure device includes an end effector supporting one or more sutures. The end effector is actuatable to position the one or more sutures in vaginal tissue. The one or more sutures are separable from the tissue closure device to enable the one or more sutures to close an opening formed in vaginal tissue.

In some embodiments, the tissue approximation device and the tissue closure device may be coupled to a handle assembly. The handle assembly may be configured to selectively actuate the tissue approximation device and the tissue closure device.

In certain embodiments, the vaginal tissue closure system may further include a vacuum source in communication with the suction aperture and may configured to generate the negative pressure applied by the suction aperture to vaginal tissue.

In some embodiments, the tissue approximation device and the tissue closure device may be separate and independent instruments.

In various embodiments, the end effector of the tissue closure device may include one or more light emitting diodes.

In certain embodiments, the end effector of the tissue closure device may include a first jaw member and a second jaw member. The first and second jaw members may be positionable between open and closed positions to selectively grasp vaginal tissue. The first jaw member may support one or more sutures. The one or more sutures may have a distal end portion. The second jaw member may support a capture tool defining a receiving aperture. The receiving aperture may be configured to capture the distal end portion of the one or more sutures when the first and second jaw members are disposed in the closed position so that the distal end portion of the one or more sutures separate from the first jaw member as the first and second jaw members move from the closed position to the open position.

In some embodiments, the one or more sutures may include an end loop defined therein through which the one or more sutures can be threaded to facilitate tying of the one or more sutures to vaginal tissue.

In various embodiments, the one or more sutures may include a plurality of sutures simultaneously deployable from the end effector when the end effector is actuated.

In embodiments, the paddle may extend to a lip defining a distal curl configured to conform to vaginal tissue. The distal lip may define one or more slots therethrough configured to enable the one or more sutures to pass therethrough.

According to another aspect of the present disclosure, a vaginal tissue closure device is provided. The vaginal tissue closure device includes an end effector supporting an array of sutures. The end effector is actuatable to simultaneously position the sutures in an annular array around an opening formed in vaginal tissue in order to close the opening. Each suture of the array of sutures is configured to separate from the end effector so that the array of sutures can be tied to the vaginal tissue to maintain the opening in a closed state.

In some embodiments, each suture of the array of sutures may be coupled to a needle to pierce tissue.

In certain embodiments, each suture of the array of sutures may include an anchor. The anchor may include bioabsorbable material.

In various embodiments, each suture of the array of sutures may be barbed.

In some embodiments, the end effector may define slots that extend through a distal end portion thereof. One or more sutures of the array of sutures may include a first end portion and a second end portion. The first end portion of the one or more sutures may be positioned in a first slot of the slots and the second end portion of the one or more sutures may be positioned in a second slot of the slots.

In certain embodiments, the end effector may include one or more light emitting diodes.

In embodiments, the end effector may include a first jaw member and a second jaw member. One or both of the first or second jaw members may be movable from a first position to a second position to move the first and second jaw members between an open position and a closed position. The first jaw member may support the array of sutures in an annular array thereabout. The annular array may define an arched profile.

According to still another aspect of the present disclosure, a method of closing opened vaginal cuff tissue is provided. The method may include applying negative pressure through one or more paddles of a tissue approximation device to vaginal cuff tissue surrounding an opening defined between the vaginal cuff tissue, manipulating the one or more paddles of the tissue approximation device to approximate the vaginal cuff tissue and to position the opening in a closed state, and suturing the vaginal cuff tissue to maintain the opening of the vaginal cuff tissue in a closed state.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein:

FIGS. 4A-4D are progressive views illustrating the tissue closure system of FIG. 1 closing vaginal cuff tissue;

FIG. 10A is a perspective view of an end effector of the tissue closure device of FIG. 9;

FIG. 10B is an enlarged view of the indicated area of detail shown in FIG. 10A;

FIG. 10C is an end view of the end effector of FIG. 10A; and

FIG. 11 is a perspective view of sutures of the tissue closure device of FIG. 9 shown positioned in tissue after deployment from the tissue closure device of FIG. 9.

DETAILED DESCRIPTION

Figure 1:
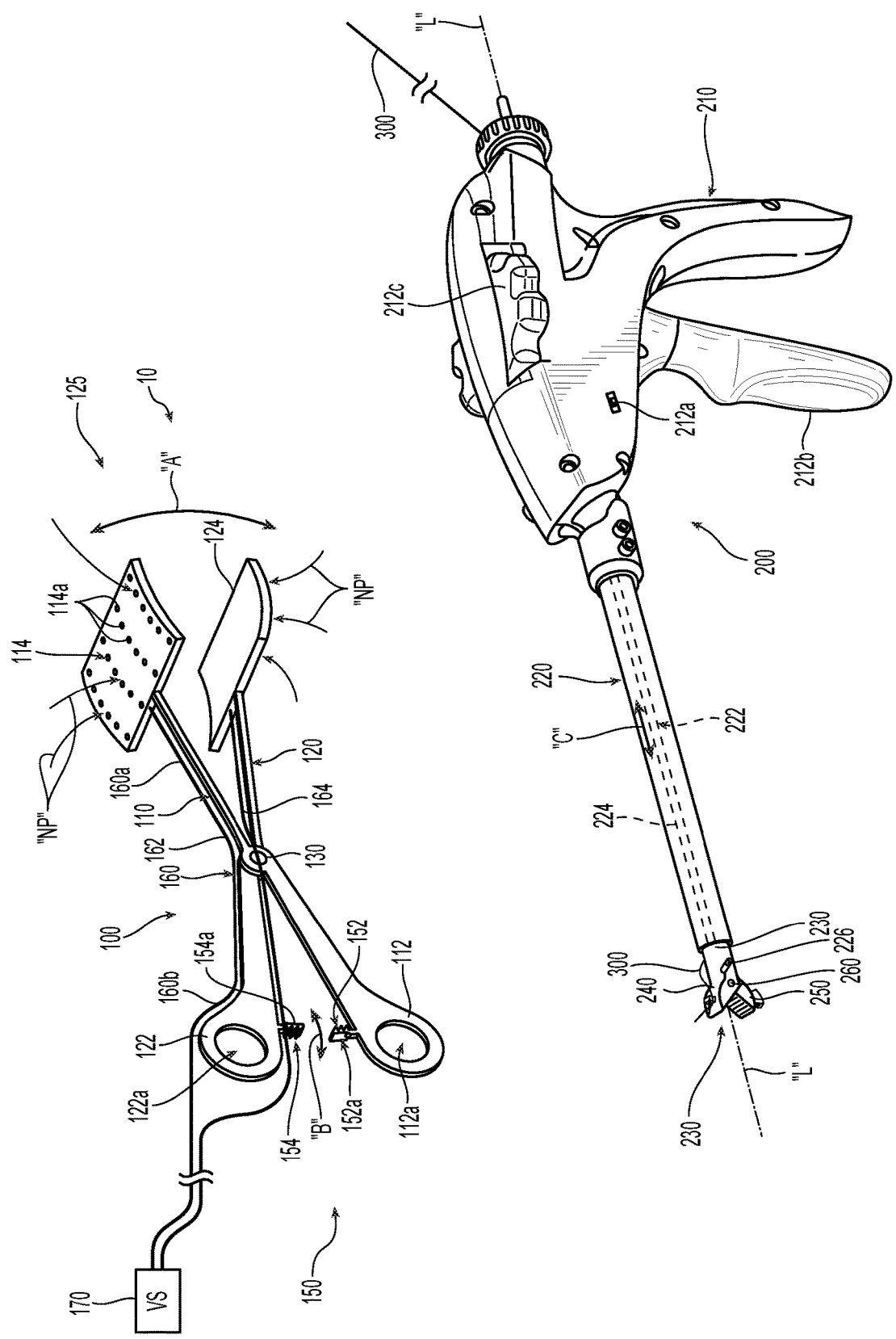
FIG. 1 is a perspective view of one embodiment of a tissue closure system in accordance with the present disclosure including an illustrative tissue approximation device and an illustrative tissue closure device.

Embodiments of the present disclosure are described in detail with reference to the drawings, in which like reference numerals designate identical or corresponding elements in each of the several views. As used herein, the term "distal" refers to that portion of structure farther from the user, while the term "proximal" refers to that portion of structure, closer to the user. As used herein, the term "clinician" refers to a doctor, nurse, or other care provider and may include support personnel. In the following description, well-known functions or constructions are not described in detail to avoid obscuring the present disclosure in unnecessary detail.

Turning now to FIG. 1, one embodiment of a vaginal tissue closure system, generally referred to as 10, is shown and includes a tissue approximation device 100 and a tissue closure device 200.

Figure 2B:
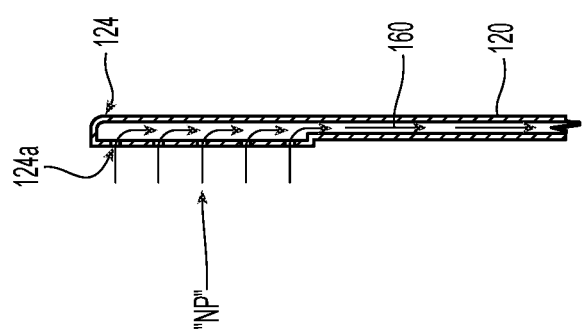
FIG. 2B is a side, cross-sectional view of a portion of the distal portion of the tissue approximation device of FIG. 2A.
Figure 2A:
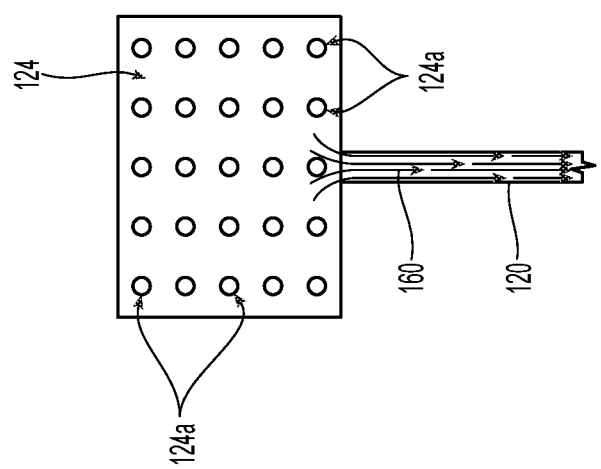
FIG. 2A is a top view of a distal portion of a tissue approximation device of the tissue closure system of FIG. 1.

With reference to FIGS. 1, 2A, and 2B, the tissue approximation device 100 of the vaginal tissue closure system 10 includes a first shaft member 110 and a second shaft member 120 that are pivotally coupled together by a pivot pin 130. The first shaft member 110 has a handle 112 at a proximal end portion thereof and a paddle 114 at a distal end portion thereof. The second shaft member 120 has a handle 122 at a proximal end portion thereof and a paddle 124 at a distal end portion thereof. The first and second paddles 114, 124 of the first and second shaft members 110, 120 are disposed in cooperative arrangement to define an end effector 125 of the tissue approximation device 100. The handle 112 of the first shaft member 110 defines an opening 112a and the handle 122 of the second shaft member 120 defines an opening 122a. The openings 112a, 122a are configured to receive a user's fingers (not shown) to facilitate pivoting of the first and second shaft members 110, 120 relative to one another, as indicated by arrows "A," to move the paddles 114, 124 between open and closed positions. In an open position, as seen in FIG. 1, the paddles 114, 124 are unapproximated or separated from one another. In a closed position (not shown), the paddles 114, 124 are approximated or in close proximity to one another (and may be in contact).

The paddle 114 of the first shaft member 110 defines suction apertures 114a in an outer surface thereof and the paddle 124 of the second shaft member 120 defines suction apertures 124a (FIG. 2A) in an outer surface thereof. The paddles 114, 124 and/or the suction apertures 114a, 124a of the first and second shaft members 110, 120 can have any suitable configuration such as circular, noncircular, and/or combinations thereof. In some embodiments, one or both of the paddles 114, 124 can be flat, curved, linear, spherical, etc., and/or combinations thereof. In certain embodiments, one or both of the paddles 114, 124 can have one or more smooth surfaces, textured surfaces, and/or combinations thereof. For example, the outer surfaces of one or both of the paddles 114, 124 can be textured to facilitate tissue gripping. In certain embodiments, one or both of the paddles 114, 124 can include one or more light emitting diodes to provide illumination for visualization and/or for facilitating placement. The one or more light emitting diodes (not shown) can be positioned, for example, on a distal end or distal end portion of one or both of the paddles 114, 124.

The tissue approximation device 100 of the vaginal tissue closure system 10 further includes a locking mechanism 150 to selectively lock the first and second shaft members 110, 120 relative to one another. The locking mechanism 150 includes a first arm 152 extending from the first shaft member 110 and a second arm 154 extending from the second shaft member 120. The first arm 152 has one or more teeth 152a and the second arm 154 has one or more teeth 154a. The teeth 152a, 154a are configured to selectively interdigitate to lock the first and second shaft members 110, 120 in one or more positions relative to one another. The first and/or second arm 152, 154 may be flexibly and/or pivotally attached, as indicated by arrows "B," to the first or second shaft members 110, 120, respectively, to enable the first and second shaft members 110, 120 to cam along one another to facilitate interdigitation and/or to selectively separate from one another once interdigitated. The one or more teeth 152a, 154a of the first and second arms 152, 154 may be configured to ratchet along one another.

The tissue approximation device 100 of the vaginal tissue closure system 10 also includes a suction conduit 160 having a distal portion 160a in fluid communication with the suction apertures 114a, 124a of the end effector 125 and a proximal portion 160b in fluid communication with a vacuum source 170. The vacuum source 170 is configured to generate negative pressure, as indicated by arrows "NP," through the suction conduit 160 and suction apertures 114a, 124a. The suction conduit 160 includes a first branch 162 coupled to the paddle 114 of the end effector 125 and a second branch 164 coupled to the paddle 124 of the end effector 125.

Figure 3:
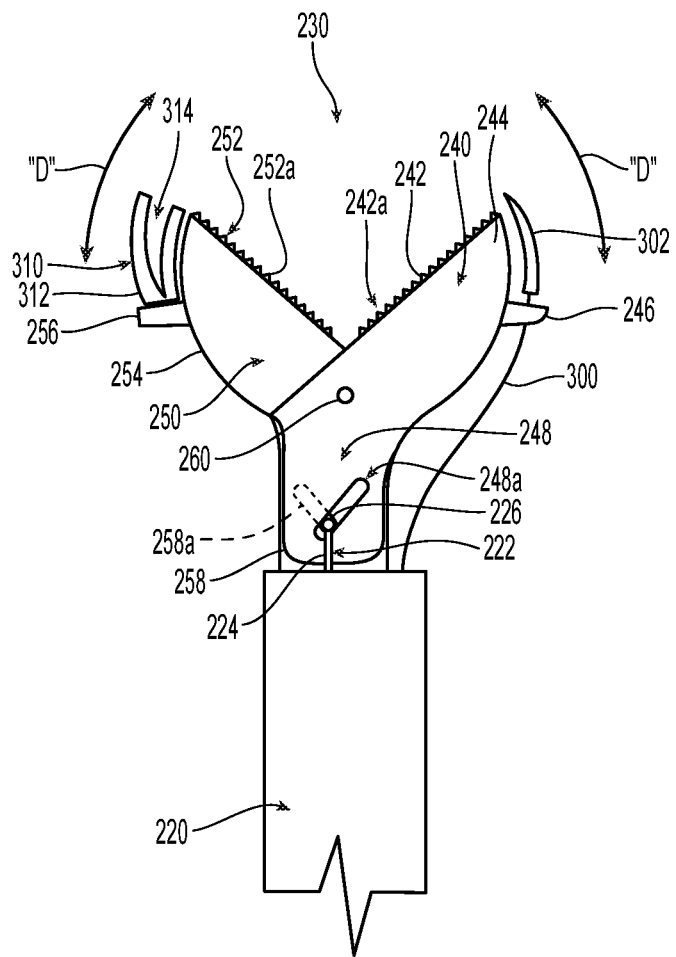
FIG. 3 is a side view of one embodiment of an end effector of the tissue closure device of the tissue closure system of FIG. 1.

With reference to FIGS. 1 and 3, the tissue closure device 200 of the vaginal tissue closure system 10 includes a handle assembly 210 with one or more actuators 212a, 212b, 212c that may include any suitable slide, knob, button, trigger or the like. The tissue closure device 200 further includes an elongated tubular body portion 220 that extends distally from the handle assembly 210 and defines a longitudinal axis "L-L" extending through proximal and distal end portions of the elongated tubular body portion 220. The elongated tubular body portion 220 includes a drive assembly 222 and supports an end effector 230 at the distal end portion thereof. The drive assembly 222 includes a drive arm 224 coupled to the handle assembly 220 at a proximal end portion thereof and a cam pin 226 coupled to the end effector 230 at a distal end portion thereof. The drive arm 224 and cam pin 226 of the drive assembly 222 are axially movable along the longitudinal axis "L-L," as indicated by arrows "C," in response to actuation of one or more of the actuators 212a-212c of the handle assembly 210 to remotely operate the end effector 230. The drive arm 224 may be in the form of a rod, tube, shaft, chain, cable, wire, and/or combinations thereof.

The end effector 230 of the tissue closure device 200 includes a first jaw member 240 and a second jaw member 250 that are pivotally coupled together about a pivot pin 260, as indicated by arrows "D" (FIG. 3) to position the first and second jaw members between open (FIGS. 4A and 4C) and closed positions (FIG. 4B). The first jaw member 240 includes an inner gripping surface 242 and an outer support surface 244. The inner gripping surface 242 includes one or more grips 242a, which may include one or more teeth, ridges, spikes, texturing, etc. to facilitate tissue gripping. The outer support surface 244 includes a suture mounting arm 246 configured to selectively support one or more sutures 300. The first jaw member 240 further includes an actuating arm 248 extending proximally therefrom.

Figure 5A:
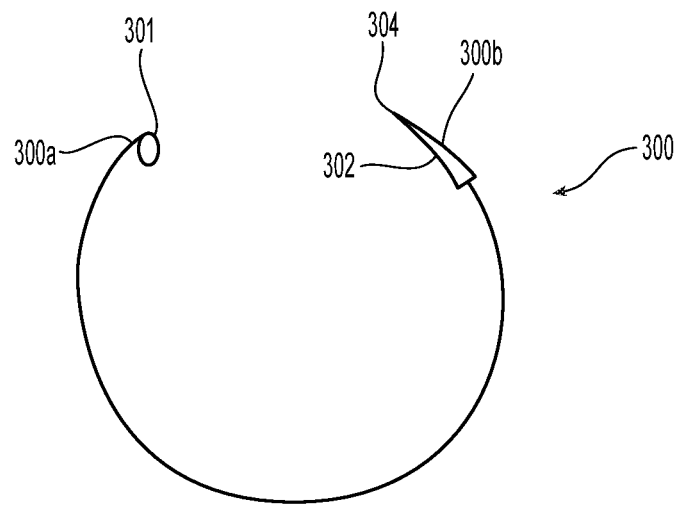
FIGS. 5A and 5B are progressive views illustrating suture of the tissue closure device of FIG. 3 being tied together.
Figure 5B:
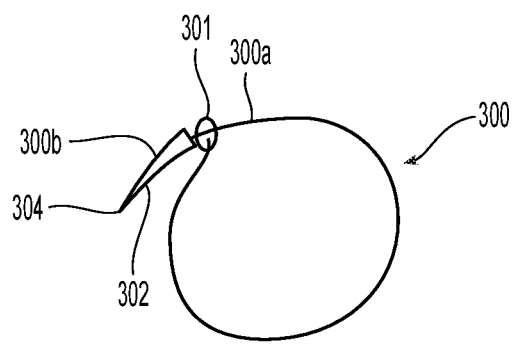

With brief reference to FIGS. 5A and 5B, each suture 300 includes a proximal end portion 300a and a distal end portion 300b. The proximal end portion 300a includes an end loop 301 and the distal end portion 300b includes a distal anchor 302 that extends to a distal tip 304. The end loop 301 of the suture 300 is configured to receive the distal end portion 300b of the suture 300. The distal anchor 302 may be in the form of a needle and may be removably coupled to the suture 300. The distal tip 304 may be sharpened.

Referring back to FIG. 3, the second jaw member 250 of the end effector 230 includes an inner gripping surface 252 and an outer support surface 254. The inner gripping surface 252 of the second jaw member 250 includes one or more grips 252a configured to engage and/or interdigitate with the grips 242a of the inner gripping surface 242 of the first jaw member 250 to facilitate tissue gripping between the first and second jaw members 240, 250. Like the grips 242a of the first jaw member 240, the grips 252a of the second jaw member 250 may include one or more teeth, ridges, spikes, texturing, etc. configured to complement and/or interdigitate with the grips 242a of the first jaw member 240. The outer support surface 254 of the second jaw member 250 includes a suture mounting arm 256 configured to selectively support one or more capture tools 310. Each capture tool 310 includes a capture body 312 defining an aperture 314 configured to receive the distal anchor 302 of one of the sutures 300. The aperture 314 may include a tapered configuration to enable the capture tool 310 to selectively capture the distal anchor 302, such as by friction fit engagement, therein. The second jaw member 250 further includes an actuating arm 258 extending proximally therefrom.

The actuating arms 248, 258 of the respective first and second jaw members 240, 250 define elongated slots 248a, 258a, respectively, configured to slidably receive the cam pin 226 of the drive assembly 222 to enable the first and second jaw members 240, 250 to move between the opened and closed positions for selectively grasping tissue such as vaginal cuff tissue "T" (FIG. 4A). The elongated slots 248a, 258a of the respective first and second jaw members 240, 250 are disposed at any suitable angle relative to the longitudinal axis "L-L" (FIG. 1), and relative each other, to facilitate pivoting movement of the first and second jaw members 240, 250. For instance, although elongated slots 248a, 258a are illustrated in a first orientation relative to one another, elongated slots 248a, 258a may be oriented in a second orientation in which respective elongated slots 248a, 258a are disposed in a mirrored or opposite relation about longitudinal axis "L-L" relative to the first orientation (e.g., elongated slots 248a, 258a are flipped 90 degrees), or any other suitable angle.

As seen in FIGS. 4A-4D, in use, for example in connection with a colpotomy or hysterectomy procedure, the end effector 125 of tissue approximation device 100 of the vaginal tissue closure system 10 is introduced transvaginally and positioned adjacent to vaginal cuff tissue "VC" that is opened (e.g., incised) or otherwise separated to define a tissue opening "TO" in the vaginal cuff tissue "VC." Previously, simultaneously, or subsequently to the transvaginal introduction of the tissue approximation device 100, the tissue closure device 200 can be transvaginally introduced. Regardless of when the tissue closure device 200 is introduced, with the tissue approximation device 100 transvaginally introduced, the first and second paddles 114, 124 of the end effector 125 of the tissue approximation device 100 are positioned on opposite sides of the tissue opening "TO" adjacent to the vaginal cuff tissue "VC." The first and second paddles 114, 124 may be positioned so that flaps "F1" and "F2" of the vaginal cuff tissue "VC" partially overhang the first and second paddles 114, 124, respectively, so that the flaps "F1" and "F2" are disposed (e.g., hang) between the first and second paddles 114, 124. The vacuum source 170 (FIG. 1) is configured to apply negative pressure "NP" through the suction apertures 114a, 124a of the first and second paddles 114, 124 of the end effector 125 so that the opposed sides of the vaginal cuff tissue "VC" stick, via the negative pressure "NP" (e.g., suction forces), to the respective first and second paddles 114, 124 of the end effector 125.

With the opposed sides of the vaginal cuff tissue "VC" retained by negative pressure against the end effector 125 of the tissue approximation device 100, as seen in FIG. 4A, the handles 112, 122 of the first and second shaft members 110, 120 of the tissue approximation device 100 can then be actuated to approximate the first and second paddles 114, 124 of the end effector 125. As the first and second paddles 114, 124 of the end effector 125 approximate, the flaps "F1" and "F2" of the vaginal cuff tissue "VC" approximate one another. With the end effector 230 of the tissue closure device 200 positioned adjacent to the flaps "F1" and "F2" of the vaginal cuff tissue "VC" (e.g., between the first and second paddles 114, 124), the first and jaw members 240, 250 of the end effector 230 of the tissue closure device 200 can be pivoted toward the closed position, as seen in FIG. 4B, upon axial translation (e.g., distally) of the cam pin 226 of the drive assembly 222 through the elongated slots 248a, 248b of the end effector 230 of the tissue closure device 200. As the first and second jaw members 240, 250 of the end effector 230 move to the closed position, the first and second jaw members 240, 250 grasp the flaps "F1" and "F2" of the vaginal cuff tissue "VC" and further approximate and/or compress the flaps "F1" and "F2" together. Closing movement of the first and second jaw members 240, 250 causes the distal anchor 304 to pass through the compressed flaps "F1" and "F2" of the vaginal cuff tissue "VC." The distal anchor 304 is advanced so that the suture 300 is also drawn through the flaps "F1" and "F2" of the vaginal cuff tissue "VC." Once through the flaps "F1" and "F2" of the vaginal cuff tissue "VC," the distal anchor 304 is received and captured within the aperture 314 of the capture tool 310.

As seen in FIG. 4C, the first and second jaw members 240, 250 can then be moved toward the open position upon axial translation (e.g., proximally) of the cam pin 226 of the drive assembly 222 through the elongated slots 248a, 248b of the end effector 230 of the tissue closure device 200. With the distal anchor 302 of the suture 300 captured by the capture tool 310 and the suture 300 mounted to the flaps "F1" and "F2" of the vaginal cuff tissue "VC," the tissue closure device 200 can be transvaginally removed with the distal anchor 302 and capture tool 310 connected, as seen in FIG. 4D. Once the tissue closure device 200 of the vaginal closure system 10 is removed, the distal anchor 302 can be manually separated from the capture device 310 (e.g., ex vivo while the suture 300 is still connected to the flaps "F1" and "F2" of the vaginal cuff tissue "VC") so that the distal anchor 302 (and/or distal end portion of the suture 300) can be threaded through its end loop 301 (see FIGS. 5A and 5B) and tied (e.g., tightened, knotted, trimmed, etc.) to the joined flaps "F1" and "F2" of the vaginal cuff tissue "VC" to maintain the vaginal cuff tissue "VC" closed. In some embodiments, end loop 301 can be positioned around capture device 310. The distal anchor 302 can be severed from the suture 300, as desired. Any knots tied in the suture 300 can be effectuated ex vivo and/or in vivo, and may be effectuated with a knot pusher such as Medtronic's ENDO SLIDE' (not shown).

The tissue approximation device 100 of the vaginal closure system 10 may be transvaginally removed before, with, or after the tissue closure device 200, as desired.

Alternatively, the tissue approximation device 100 of the vaginal closure system 10 may be maintained in position so that one or more additional sutures 300 can be mounted to the tissue closure device 200 for repeating the above described suturing process as desired. Alternately, and or additionally, a different or additional tissue closure device 200 can be transvaginally inserted to repeat the above described suturing process, as desired.

Figure 6:
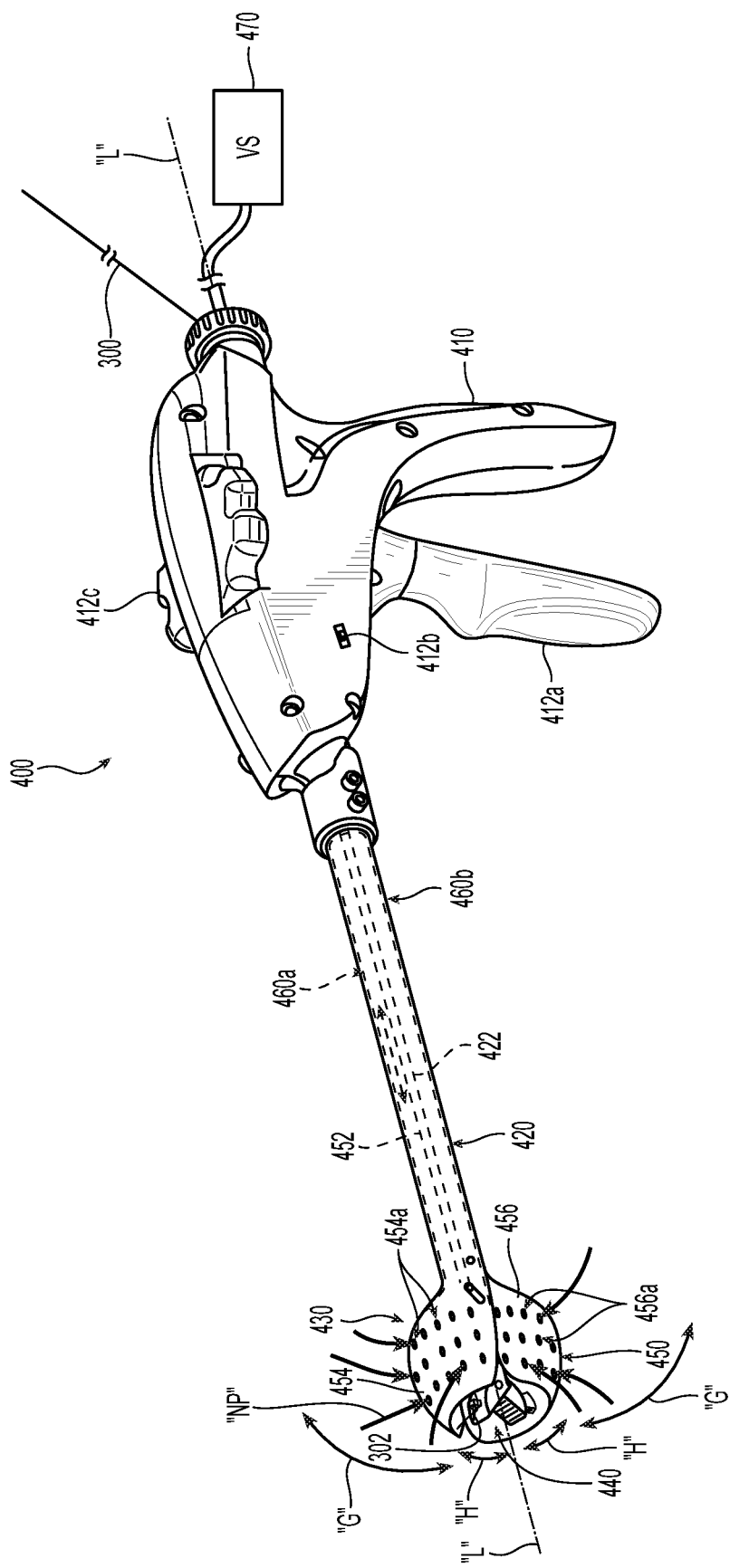
FIG. 6 is a perspective view of another embodiment of a tissue closure device in accordance with the present disclosure.

Turning now to FIG. 6, another embodiment of a tissue closure system or device is generally referred to as 400. The tissue closure device 400 incorporates respective features of the entire tissue closure system 10 (e.g., the tissue closure device 200 and the tissue approximation device 100) into a single device.

The tissue closure device 400 includes a handle assembly 410 with one or more actuators 412a, 412b, 412c that may include any suitable slide, knob, button, trigger or the like. The tissue closure device 400 further includes an elongated tubular body portion 420 that extends distally from the handle assembly 410 and defines a longitudinal axis "L-L" extending through proximal and distal end portions of the elongated tubular body portion 420. The elongated tubular body portion 420 supports an end effector 430 at the distal end portion thereof. The end effector 430 includes a tissue closure portion 440 and a tissue approximation portion 450 that surrounds the tissue closure portion 440. The tissue closure portion 440 is substantially structurally and operationally similar to the end effector 230 of the tissue closure device 200. The tissue approximation portion 450 is structurally similar to the end effector 125 of the tissue approximation device 100, but may be operatively similar to the end effector 230 of the tissue closure device 200 (e.g., cam pin and slot driven).

The elongated tubular body portion 420 further includes a first drive assembly 422 and a second drive assembly 452 that are operatively coupled to the handle assembly 410 to selectively remotely actuate the end effector 430.

The first drive assembly 422 of the tissue closure device 400 is secured to the handle assembly 410 at the proximal end portion thereof and operatively coupled to one or more of the actuators 412a, 412b, 412c of the handle assembly 410. In particular, the first drive assembly 422 is configured to remotely actuate the tissue closure portion 440 of the end effector 430 (as illustrated by arrows "G") in response to actuation of one or more of the actuators 412a, 412b, 412c of the handle assembly 410 (e.g., structurally and operationally similar to the drive assembly 222 of the tissue closure device 200).

The second drive assembly 452 of the tissue closure device 400 is secured to the handle assembly 410 at the proximal end portion thereof and operatively coupled to one or more of the actuators 412a, 412b, 412c of the handle assembly 410. The second drive assembly 452 is configured to remotely actuate the tissue approximation portion 450 (as illustrated by arrows "H") of the end effector 430 of the tissue closure device 400 in response to actuation of one or more of the actuators 412a, 412b, 412c of the handle assembly 410 (e.g., structurally and operationally similar to the drive assembly 222 of the tissue closure device 200). Specifically, instead of moving paddles between open and closed positions to approximate and/or unapproximate tissue upon pivoting movement of a pair of movable handles, such as detailed above in connection with tissue approximation device 100, the paddles 454, 456 of the tissue approximation portion 450 of the end effector 430 are movable relative to one another in response to actuation of the second drive assembly 452. Actuation of one or more of the actuators 412a, 412b, 412c of the handle assembly 420 causes the second drive assembly 452 to axially translate relative to the elongated tubular body 420 and the paddles 454, 456 of the tissue approximation portion 450 to move between open and closed positions.

Similar to the tissue approximation device 100, the tissue approximation portion 450 of the tissue closure device 400 includes suction conduits 460a, 460b in fluid communication with suction apertures 454a, 456a defined in the respective paddles 454, 456 of the tissue approximation portion 450. The suction conduits 460a, 460b are disposed in fluid communication with a vacuum source 470 configured to generate negative pressure "NP" (see FIG. 4A) such that movement of the paddles 454, 456 of the tissue approximation portion 450 between open and closed positions causes tissue secured thereto (e.g., via suction) to move between approximated and/or unapproximated positions.

In some embodiments, the vacuum sources of the present disclosure may be in fluid communication with a storage or drainage container to facilitate removal of bodily discharge such a blood, etc. that is removed from the patient's body through the suction conduit.

In general, the tissue closure device 400 is utilized in a substantially similar manner to the tissue closure system 10; however, the tissue approximation portion 450 and the tissue closure portion 440 are operated by a single handle assembly and are introduced and/or removed simultaneously.

Although various drive features for the end effectors of some of the presently disclosed embodiments are generally described herein with a cam-pin-and-slot type configuration, the drive features for the end effectors of the presently disclosed embodiments can be configured to include any suitable mechanical and/or electrical drive feature, such as gears (e.g., worm gear), drive screws, pulleys, cables and/or the like, to effectuate end effector opening and/or closing.

Figure 7:
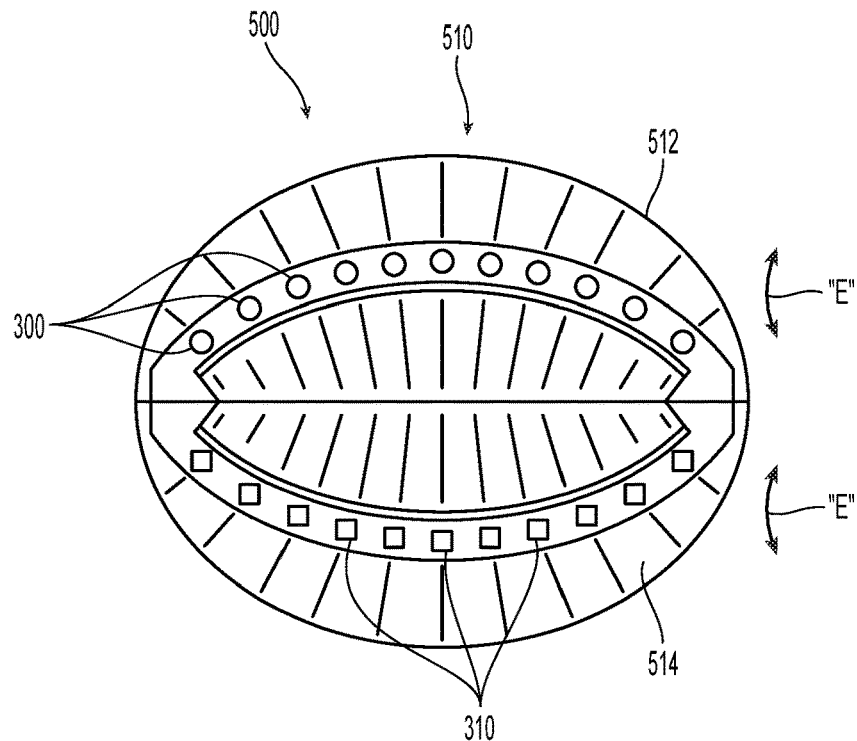
FIG. 7 is an end view of yet another embodiment of a tissue closure device in accordance with the present disclosure.

Turning now to FIG. 7, one embodiment of a tissue closure device, generally referred to 500, includes an end effector 510 having a first jaw member 512 and a second jaw member 514 that are pivotally coupled together. The first jaw member 512 of the end effector 510 supports sutures 300 arranged in an annular array (e.g., arched or semi-circular). The second jaw member 514 of the end effector 510 includes capture tools 310 arranged in an annular array complementing the annular array of sutures 300 of the first jaw member 512.

In use, the end effector 510 is movable between open (FIG. 7) and closed positions, as indicated by arrows "E," so that the array of sutures 300 can be simultaneously thrown from the first jaw member 512, and simultaneously received in the array of capture tools 310 of the second jaw member 514, as the end effector 510 of the tissue closure device 500 moves toward the closed position.

Figure 8:
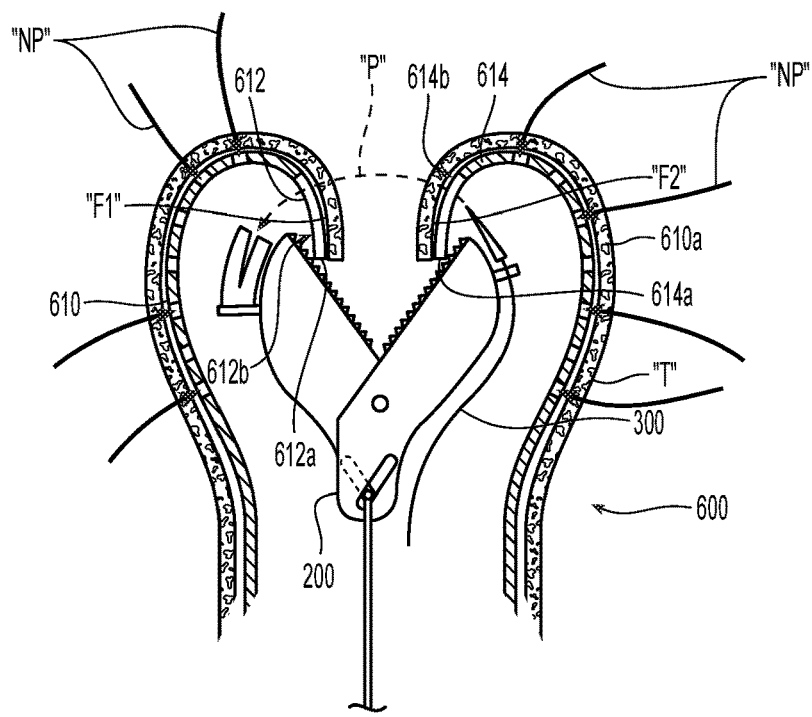
FIG. 8 is a side view, in partial cross-section, of still another embodiment of a tissue closure system in accordance with the present disclosure shown inside a vaginal cavity.

With reference to FIG. 8, another embodiment of a tissue closure system, generally referred to as 600, is provided. The tissue closure system 600 includes the tissue closure device 200 and another embodiment of a tissue approximation device 610. The tissue approximation device 610 is similar to the tissue approximation device 100, but includes an end effector 610a with paddles 612, 614. The paddles 612, 614 include lips 612a, 614a that curl inwardly and are arranged to hold the flaps "F1" and "F2" of tissue "T" (e.g., vaginal cuff tissue) in a throwing path "P" of the suture 300 defined by the tissue closure device 200. The lips 612a, 614a define one or more slots 612b, 614b therethrough. The slots 612b, 614b are positionable along the throwing path "P" of the suture 300 so that the suture 300 does not get stuck in the tissue approximation device 610 while the first and second jaw members of the tissue closure device 200 close.

Although the tissue closure device 200 and the tissue approximation device 610 of the tissue closure system 600 are described as independent devices or instruments, the tissue closure system 600 can be provided as a single device similar to the tissue closure device 400.

Figure 9:
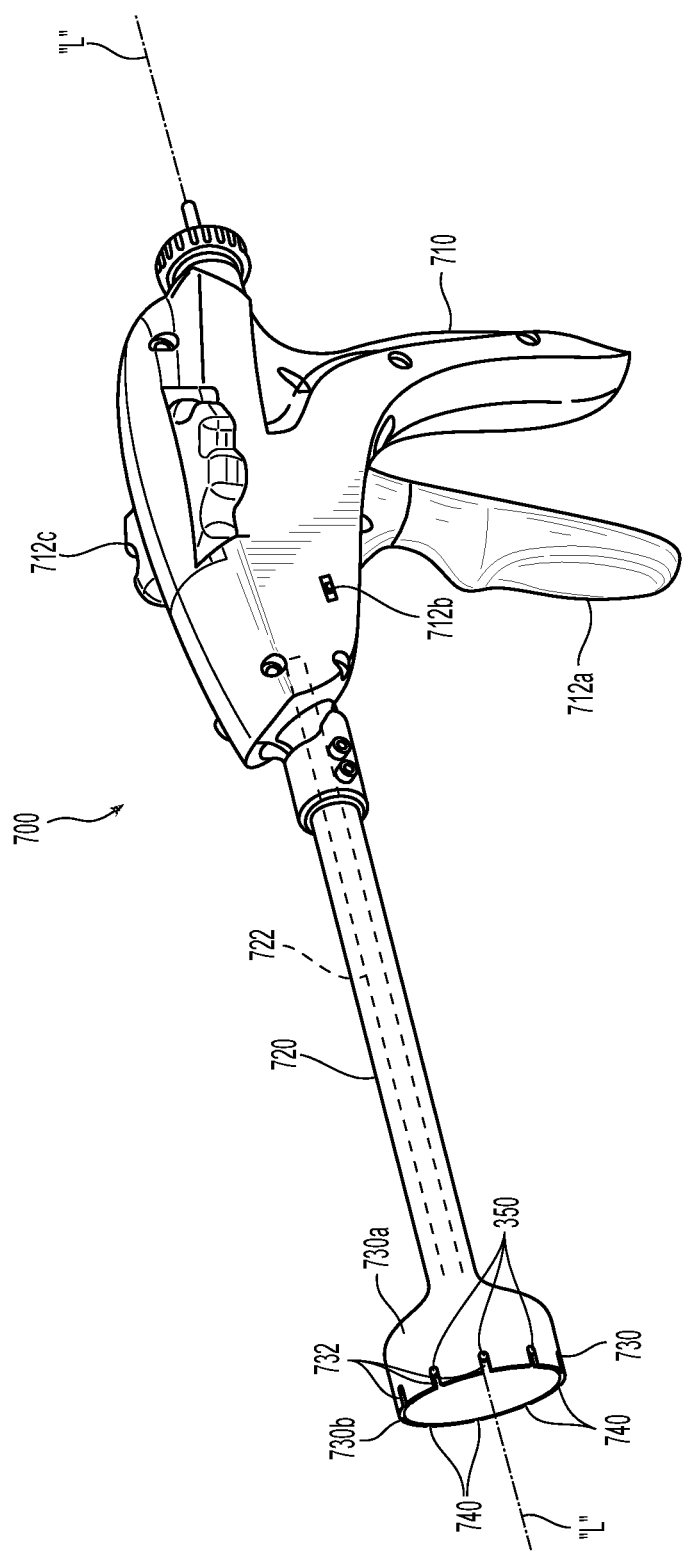
FIG. 9 is a perspective view of another embodiment of a tissue closure device in accordance with the present disclosure.

Turning now to FIGS. 9-11, yet another embodiment of a tissue closure device, generally referred to as 700, may be utilized as a uterine manipulator and/or vaginal cuff closure device. The tissue closure device 700 includes a handle assembly 710 with one or more actuators 712a, 712b, 712c. The tissue closure device 700 further includes an elongated tubular body portion 720 that extends distally from the handle assembly 710 and defines a longitudinal axis "L-L" extending through proximal and distal end portions of the elongated tubular body portion 720. The elongated tubular body portion 720 includes a drive assembly 722 operatively coupled to the handle assembly 710 at the proximal end portion thereof and an end effector 730 at the distal end portion thereof.

The drive assembly 722 of the tissue closure device 700 is operatively coupled to one or more of the actuators 712a-712c of the handle assembly 710 to remotely operate the end effector 730 upon actuation of one or more of the actuators 712a-712c. The drive assembly 722 includes an annular array of drive needles 724 extending distally therefrom and operatively coupled to an array of sutures 350, described in greater detail below. The needles 724 extend to distal tips 724a that may be sharpened. The needles 724 may be formed of any suitable rigid material, such as a metallic and/or polymeric material.

As seen in FIGS. 10A-10C, the end effector 730 of the tissue closure device 700 is in the form of a colpotomy cup that may be utilized to present the location of the vaginal fornix to facilitate transection of the uterus/cervix from the vaginal canal. The end effector 730 also is configured to facilitate creation of a colpotomy and/or transection of the uterus.

The end effector 730 defines an array of spaced-apart slots 732 that support the sutures 350. Each slot 732 extends through a distal end portion 730a of the end effector 730 and a distal end face 730b of the end effector 730 to enable the sutures 350 to be selectively separated or deployed from the slots 732 as the needles 724 are deployed therefrom.

In some embodiments, the end effector 730 may include light emitting diodes 740 to facilitate visualization and/or to provide suture guides. In certain embodiments, the light emitting diodes 740 (FIGS. 9, 10C) may be positioned in an annular array around the distal end portion 730b and/or distal end face 730a of the end effector 730.

Each suture 350 of the end effector 730 includes a first end portion 352 and a second end portion 354 that are supported in diametrically opposed slots 732a, 732b (FIG. 10C) to create apposition between the first and second end portions 352, 354 of the suture 350. In some embodiments, the opposed slots 732a, 732b defined in the end effector 730 are disposed in mirrored relationship to facilitate apposition between the first and second end portions 352, 354 of the suture 350. The first and second end portions 352, 354 of each suture 350 support anchors 352a, 354a, respectively, that are configured to prevent retraction of first and second end portions 352, 354 of the suture 350 through tissue "T" (FIG. 11).

With reference to FIG. 11, in use, the tissue closure device 700 (FIG. 9) is transvaginally introduced and positioned adjacent to vaginal tissue "T" (e.g., vaginal cuff tissue). The needles 724 of the tissue closure device 700 are configured to move between a retracted position (FIG. 9) and an extended position (FIG. 10A) upon axial advancement of the drive assembly 722, as indicated by arrows "F" (FIG. 10A), in response to actuation of one or more of the actuators 712a-712c of the handle assembly 710 of the tissue closure device 700. In the retracted position, the needles 724 of the tissue closure device 700 and the anchors 352a, 354a of the sutures 350 are supported in the slots 732 of the end effector 730. In the retracted position, the end effector 730 can be utilized, for example, as a uterine manipulator and/or to facilitate creation of a colpotomy. In the extended position, the needles 724 of the tissue closure device 700 and the anchors 352a, 354a (FIG. 10A) of the sutures 350 are deployed from the slots 732 of the end effector 730 to enable securement of the sutures 350 to tissue "T."

As the needles 724 of the tissue closure device 700 are deployed (individually, in groups, entirely, sequentially, and/or simultaneously) from the end effector 730 of the tissue closure device 700, the distal tips 724a of the needles 724 pierce through the fornix "FX" of the tissue "T" so that the anchors 352a, 354a of each respective suture 350 secure the first and second end portions 352, 354 of each respective suture 350 to the fornix "FX" at diametrically opposed locations "L1" and "L2," respectively, about the fornix "FX." Once the suture 350 is anchored to the fornix "FX," the needles 724 of the tissue closure device 700 can be retracted through the anchors 352a, 354a of the sutures 350 and separated from the sutures 350. The tissue closure device 700 can then be retracted and/or removed such that the sutures 350 separate from the slots 732 of the end effector 730. The clinician can then perform a colpotomy procedure to create a vaginal cuff. The end effector 730 may be utilized as a guide to create the colpotomy circumferentially thereabout. With the sutures 350 anchored in position via anchors 352a, 354a of the sutures 350, the sutures 350 can be tied (e.g., tightened, knotted, trimmed, etc.) to the tissue "T" (e.g., vaginal cuff tissue) to close the tissue "T," as desired.

Any of the presently disclosed sutures, such as sutures 300, 350, and/or components thereof (e.g., the anchors 352a, 354a) may be bioabsorbable. In certain embodiments, the sutures, or portions thereof, may be color coded to ensure that the proper ends of the respective sutures are tied together. In some embodiments, the presently disclosed sutures 300, 350 may include one or more barbs 356 (FIG. 10B), which may be oriented in different and/or opposite directions on different ends of the respective sutures. In certain embodiments, the one or more barbs 356 may be utilized instead of the anchors 352a, 354a. For a more detailed description of barbed sutures and materials thereof, reference can be made, for example, to U.S. Pat. No. 9,241,709, the entire contents of which are incorporated by reference herein. In certain embodiments, the presently disclosed sutures 300, 350 include Medtronic's V-LOC® technology.

Advantageously, some of the presently disclosed embodiments of tissue closure devices and/or systems provide structure to enable multiple sutures to be thrown at once and at predetermined positions (e.g., spacing relative to the other sutures). This advantage limits the number of iterations or bites to which the tissue is exposed and occurrence of improper spacing between sutures, thereby limiting tissue damage, limiting risks of undesirable tissue re-opening, increasing reliability of tissue apposition, and promoting tissue healing.

In some embodiments of the presently disclosed tissue closure devices, a knife or cutting surface may be provided at any suitable location on the end effectors thereof to facilitate a cutting or trimming (e.g., manual or automated) of any of the presently disclosed sutures.

Securement of any of the components of the presently disclosed devices may be effectuated using known securement techniques such welding, crimping, gluing, fastening, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely control the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A tissue closure system, comprising:
   a vacuum source;
   a tissue approximation device having a paddle including a suction aperture defined therein, the suction aperture in fluid communication with the vacuum source to apply negative pressure to tissue to maintain the tissue in close proximity to the paddle; and
   a tissue closure device including movable jaw members supporting at least one suture, the jaw members actuatable between open and closed positions to selectively grasp the tissue and to position the at least one suture in the tissue for closing an opening formed in the tissue.

2. The tissue closure system of claim 1, wherein the tissue approximation device and the tissue closure device are coupled to a handle assembly, the handle assembly configured to selectively actuate the tissue approximation device and the tissue closure device.

3. The tissue closure system of claim 1, wherein the jaw members are pivotably coupled together.

4. The tissue closure system of claim 1, wherein the tissue approximation device and the tissue closure device are separate and independent instruments.

5. The tissue closure system of claim 1, wherein at least one of the jaw members includes a light emitting diode.

6. The tissue closure system of claim 1, wherein the jaw members include a first jaw member and a second jaw member, the first jaw member supporting the at least one suture.

7. The tissue closure system of claim 1, wherein the second jaw member supports a capture tool defining a receiving aperture, the receiving aperture configured to capture the at least one suture.

8. The tissue closure system of claim 1, wherein the at least one suture includes an end loop defined therein through which the at least one suture can be threaded to facilitate tying of the at least one suture to tissue.

9. The tissue closure system of claim 1, wherein the at least one suture includes a plurality of sutures, each suture of the plurality of sutures being simultaneously deployable.

10. The tissue closure system of claim 1, wherein the paddle extends to a lip defining a distal curl configured to conform to tissue, the distal lip defining at least one slot therethrough configured to enable the at least one suture to pass therethrough.

11. A method of closing opened vaginal cuff tissue, the method comprising:

applying negative pressure through at least one paddle of a tissue approximation device to vaginal cuff tissue surrounding an opening defined between the vaginal cuff tissue;

manipulating the at least one paddle of the tissue approximation device to approximate the vaginal cuff tissue and position the opening in a closed state; and suturing the vaginal cuff tissue to maintain the opening of the vaginal cuff tissue in a closed state.

\* \* \* \* \*